Figure 1:
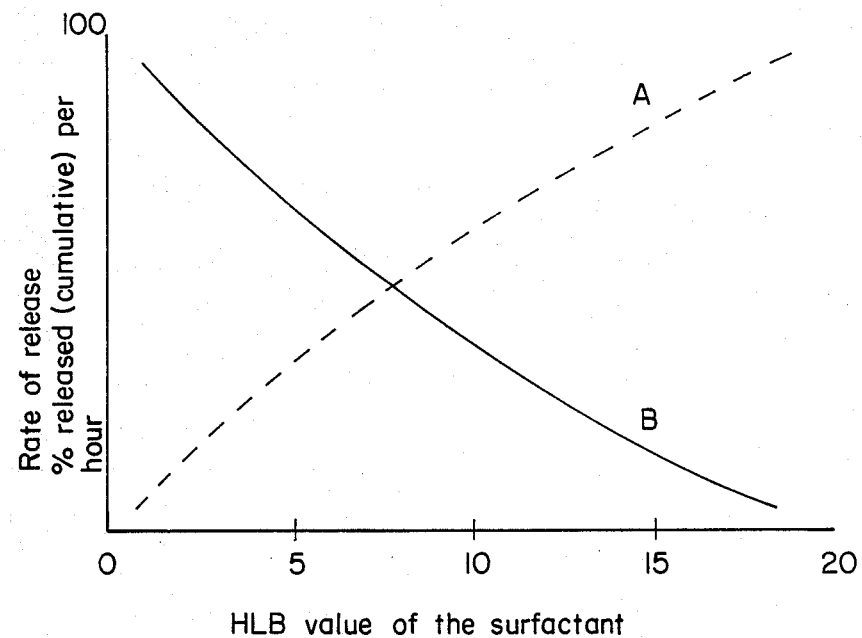

United States Patent [19]

Seth

[11] Patent Number: 4,795,643
[45] Date of Patent: Jan. 3, 1989

[54] MEDICAMENT WITH A DELAYED RELEASE OF ACTIVE INGREDIENT

[75] Inventor: Pawan Seth, Oberwil, Switzerland

[73] Assignee: Mepha AG Dornacherstrasse 114, Aesch, Switzerland

[21] Appl. No.: 67,148

[22] Filed: Jun. 29, 1987

[30] Foreign Application Priority Data

Feb. 2, 1987 [CH] Switzerland ............................ 355/87

[51] Int. Cl.⁴ ................................................ A61K 9/64
[52] U.S. Cl. .................................... 424/456; 424/457; 424/455
[58] Field of Search ............... 424/456, 452, 455, 457, 424/499, 501, 462

[56] References Cited

U.S. PATENT DOCUMENTS

| | | | |
|---|---|---|---|
| 2,990,333 | 6/1961 | Graham | 424/456 |
| 4,428,927 | 1/1984 | Ebert et al. | 424/456 X |
| 4,450,877 | 5/1984 | Walker et al. | 141/1 |
| 4,486,412 | 12/1984 | Shah et al. | 424/156 |
| 4,539,199 | 9/1985 | Orbán et al. | 424/456 |
| 4,663,149 | 5/1987 | Eckenhoff et al. | 424/452 |
| 4,681,765 | 7/1987 | Guley | 424/456 |

FOREIGN PATENT DOCUMENTS

3511236 10/1985 Fed. Rep. of Germany ...... 424/456
1242547 8/1971 United Kingdom .

*Primary Examiner*—Thurman K. Page
*Attorney, Agent, or Firm*—Birch, Stewart, Kolasch & Birch

[57] ABSTRACT

In addition to the active ingredient, the capsules contain a nonionic surfactant consisting of a polyglycol ester or ether having hydrophilic and lipophilic portions, and an organic polymer which is capable of forming a free-flowing composition with the active ingredient and the surfactant. The essential point for the delay in release is the matching of the water-solubility of the active ingredient and the hydrophilic/lipophilic character (HLB value) of the surfactant as follows:

| | |
|---|---|
| water-insoluble | HLB value above 16; |
| sparingly soluble | HLB value between 10 and 16; and |
| water-soluble | HLB value below 10. |

22 Claims, 1 Drawing Sheet

Water-insoluble active ingredients

Water-soluble active ingredients

MEDICAMENT WITH A DELAYED RELEASE OF ACTIVE INGREDIENT

The present invention relates to a medicament which is in the form of hard gelatin capsules and exerts its effect in the organism for a long time as a result of delayed release of the active ingredient.

Various medicaments and pharmaceutical preparations which are in the form of gelatin capsules with a delayed action or can be presented in this form were already known. Thus, German application No. 3,400,106 describes pharmaceutical formulations with a controlled release of medicament; in addition to the medicament, they contain one or more physiologically acceptable polymers and a lipophilic and/or hydrophilic solvent or swelling agent for the polymer or polymers. The formulation can be in any desired pharmaceutical form, and therefore, inter alia, also in the form of capsules. The polymers can be polysaccharides, proteins or polyolefins. Paraffins, oils and fats can be used as lipophilic solvents or swelling agents and water, alcohols, glycols and $C_1$-$C_6$-carboxylic acids can be used as hydrophilic solvents or swelling agents; the examples contain glycerol, polyethylene glycols or liquid paraffin.

European application No. 1,822 describes the production of pharmaceutical preparations in the form of hard gelatin capsules. The rigid shells are filled with a liquid excipient which contains the active ingredient and solidifies in the shell when cooled and left to stand, to give a solid composition or a gel. A water-soluble melt composition with a solidification point of 3020 to 60° C. or a thixotropic gel, in particular Macrogol ethers, such as polyethylene glycols, Macrogol esters, such as Polyoxyl 40 stearate, polysorbates (polyoxyethylene sorbitan fatty acid esters), sorbitan esters, polyvinyl alcohol sucrose esters and polyacrylic acids (for example Carbopol ®), is used as the liquid excipient. If the contents of the capsule are to be in the form of a thixotropic gel, they contain, for example, hydrogenated castor oil or colloidal silicon dioxide as a gelling agent.

French patent specification No. 7,955 M also relates to capsules with a delayed action. They contain a solution or a liquid or free-flowing suspension of the active ingredient and, in a water-soluble or water-insoluble excipient, a substance which is insoluble in water or dissolves slowly in water, and also a solubilizing agent or surfactant which is capable of forming an emulsion of the oil-in-water type. The water-insoluble substance forms a foam with the juices of the gastrointestinal tract, from which the active ingredient slowly diffuses out. Polyvinyl compounds, polycarbonates, polystyrene, cellulose derivatives, polyacrylic acids, waxes, fats, higher alcohols, silicone resins and the like are suitable for this. Polyethylene glycols, alcohols, esters, mixtures of castor oil and ethanol or polyethylene glycol, mixtures of peanut oil and polyoxyethylene castor oil and mixtures of paraffin oil and sorbitan esters can be used as excipients.

The documents summarized here are particularly representative of the prior art in the field of the present invention. All three are quite general proposals which are intended for use under all circumstances and in all cases: they contain, in fact, no restrictions, conditions or selection in respect of the nature or quality of the active ingredients to be introduced into gelatin capsules with a delayed action. In particular, no distinctions are made as to whether the active ingredients are water-soluble or hydrophilic, or water-insoluble or lipophilic.

However, the fact that the physico-chemical properties of the active ingredients play a decisive role in the selection of the suitable auxiliaries requires no further discussion. It is of course not irrelevant whether the active ingredient in question is readily soluble, slightly soluble or even insoluble in water and instead can readily be dissolved in the lipids. Such fundamental differences are of course all the more significant, the larger the amount of active ingredient to be incorporated in the capsules, i.e. if not just a few percent but, for example, up to 20 or 40% of the contents of the capsules is made up by the active ingredient.

According to the doctrine described above, if the intention were thus to prepare capsules with a delayed action, either the active ingredients would have to be restricted to those for which processing is demonstrated experimentally in the examples of these documents, or, for other or novel active ingredients, those auxiliaries which are suitable for the specific case would have to be selected in tedious experiments from amongst the various groups of auxiliaries of opposite properties. As a general doctrine, the methods proposed to date for any desired specific active ingredient suggest no substance-related handling; it is therefore impossible to determine the advantageous auxiliaries beforehand solely from the physico-chemical nature of the active ingredient.

Moreover, hard gelatin capsules with contents including considerable amounts of a glycol, in particular glycerol, propylene glycol or a polyethylene glycol, as is the case in the embodiment examples of German patent No. 3,400,106, European patent No. 1,822 and French patent No. 7,955 M, have been shown to have a serious disadvantage. Because of their hygroscopic nature, such glycols attract water from their environment, and thus in the present case from the capsule wall. As a result of the progressive withdrawal of water, the capsule wall becomes brittle and fragile in the course of time. This is probably one reason why the capsules according to these documents have not found acceptance in pharmaceutical practice.

Another disadvantage of the process of German patent No. 3,400,106 is that the active ingredient is introduced into a melt of the auxiliaries and is introduced into the capsules in this way, which usually requires temperatures above 100° C., and even 180° C. or more. Needless to say, the use of such high temperatures is acceptable only with active ingredients which are insensitive towards heat, otherwise they would lead to an at least partial inactivation or decomposition; in addition, the polyethylene glycols rapidly discolor to give a dark mass. Above all, however, the capsule wall is known to soften, melt and become distorted at temperatures above 70° C. [D. Cadé and co-workers, Acta Pharmaceutica Technologica 33 (1987) 97–100]; gelatin capsules must therefore be filled at lower temperatures.

Moreover, the abovementioned melts solidify at temperatures below 70° C. to give sticky compositions, which cannot be introduced into the gelatin capsules at all with conventional filling devices; special heat-stable filling devices would therefore have to be used, but these do not as yet exist.

Overall, up until now there has been a lack of a universal doctrine which would enable any desired active ingredient—that is to say also a heat-sensitive active ingredient—to be introduced into storable gelatin capsules by a route other than a purely empirical route, using the customary filling devices and achieving a precise dosage.

It has now been found that, according to the invention, any pharmaceutical active ingredient of an organic nature can be converted into the form of storable hard gelatin capsules with a delayed release of active ingredient without having to resort to carrying out a series of experiments. On the contrary, the advantageous composition can be determined beforehand if purely and simply the water-solubility of the active ingredient is focused on and the selection of the auxiliaries is based on the degree of this water-solubility; a substance or substance mixture of known HLB value (hydrophilic-lipophilic balance) and an organic polymer are the auxiliaries.

In the hard gelatin capsules according to the invention, the first essential auxiliary used is a nonionic surfactant or a mixture of such surfactants which consists of polyglycol ethers and/or esters and has both hydrophilic and lipophilic portions, and is selected in respect of the active ingredient such that its HLB value (hydrophilic-lipophilic balance)

for an active ingredient which is insoluble or slightly soluble in water is above 16, for an active ingredient which is sparingly soluble in water is between 16 and 10, and for an active ingredient which is soluble in water is less than 10, and the polymer is an organic polymer which is capable of forming a homogeneous solution or suspension with the active ingredient and the surfactant or mixture of surfactants, the solution or suspension being in the free-flowing form at about 40° to 70° C.

The capsules defined above contain the active ingredient in the form of a solution (solid solution) or a homogeneous suspension.

The invention is described in detail below.

The general definitions of the U.S. Pharmacopoeia XXI (1985), page 1441, given below, can be referred to for classification of the water-solubility:

| Description of the solubility | Parts of solvent required for 1 part of solution |
|---|---|
| very readily soluble | less than 1 |
| readily soluble | from 1 to 10 |
| soluble | from 10 to 30 |
| sparingly soluble | from 30 to 100 |
| slightly soluble | from 100 to 1000 |
| very slightly soluble | from 1000 to 10,000 |
| practically insoluble or insoluble | 10,000 and more |

For simplification, only the terms soluble, sparingly soluble and insoluble will be used here; it goes without saying, however, that the finer classification can also be used and the HLB value of the surfactant can be selected accordingly.

Surfactants are in general characterized by the HLB value (hydrophilic-lipophilic balance). A surfactant of high HLB value—for example 12 to 20—is hydrophilic, and a surfactant of low HLB value, for example less than 7, is lipophilic.

For surfactants of one and the same series amongst the esterified polyethylene glycols, for example the polyethylene glycol distearates or mono- or dipalmitostearates, the HLB value depends on the molecular weight of the molecule. Quite generally, the HLB value increases if the molecular weight increases. Thus, for example, polyethylene glycol 400-palmitostearate with an HLB value of 11 to 12 has a more powerful hydrophilic character than polyethylene glycol 300-distearate with an HLB value of 9 to 10.

The HLB values of the surfactants are additive, so that the required HLB value can also be achieved by mixing two surfactants of different HLB values; in fact, the HLB value of the system and its miscibility with the organic polymer to form a liquid composition is decisive. For a mixture of two different surfactants, the final HLB value can be calculated as follows:

$$\text{Final } HLB \text{ value} = \frac{X \cdot HLB(1) + Y \cdot HLB(2)}{X + Y}$$

X, Y: content of one or other of the surfactants in the mixture
HLB(1): HLB value of the first surfactant
HLB(2): HLB value of the second surfactant The polyglycol derivatives to be used as nonionic surfactants can be, inter alia, condensation products of hydrophobic compounds, such as fatty acids or fatty alcohols or sorbitan fatty acid esters, with polyoxyethylene glycols; these condensation products are prepared by oxyethylation of the hydrophobic compounds mentioned by known processes. The processes themselves and the products obtained are described, in particular, in "Ullmanns Encyklopädie der technischen Chemie" ("Ullmann's Encyclopedia of Industrial Chemistry"), 4th edition, Volume 22, page 488 et seq. (Verlag Chemie GmbH, Weinheim FRG 1982).

Suitable examples of the abovementioned polyoxyethylene glycol esters and ethers are polyoxyethylene glycol 400-palmitostearate with an HLB value of 11 to 12 and the corresponding compounds of molecular weight 4000 and 1500 with an HLB value above 19 or 17 respectively, and furthermore polyoxyethylene glycol 300-distearate with an HLB value of 9 to 10, the laurate, palmitate, stearate and oleate of sorbitan etherified with 4 mol of polyoxyethylene glycol (for example the polysorbates, Tween ® of ICI America Inc., Atlas Chemical Division, Wilmington Del., USA and the like) and the polyoxyethylene glycol ethers of lauryl alcohol, cetyl alcohol, stearyl alcohol and oleyl alcohol (for example the product Brij ® of Atlas Chemie GmbH, Essen FRG). Preferred nonionic surfactants are the polyoxyethylene glycol fatty acid esters.

The organic polymer is selected according to the nonionic surfactant used so that, with this and the active ingredient, it forms a homogeneous composition which is free-flowing at about 50° to 60° C. This polymer can be, in particular, methyl polyacrylate, methyl polymethacrylate, for example the commercial products Eudragit®S 100 or RS PM from Röhm Pharma GmbH (Darmstadt, FRG), or ethylcellulose or methylcellulose. It is also possible to use a mixture of two or more of these compounds as long as the rheological properties of the composition formed are retained. As is known, the organic polymers mentioned are not accessible to enzymatic biological degradation.

According to a particularly advantageous embodiment of the invention, the active ingredient makes up about 1 to 60% by weight of the contents of the capsule, the surfactant about 30 to 90% by weight and the polymer about 1 to 45% by weight.

Depending on the nature of the active ingredient used, it may be appropriate to add to the composition envisaged as the contents of the capsule an antioxidant or stabilizer, for example tert.-butyl-4-methoxyphenol (BHA), 2,6-di-tert.-butyl-4-methylphenol (butylhydroxytoluene, BHT), octyl gallate, dodecyl gallate, lactic acid or its sodium salt, the methyl, ethyl, propyl or butyl ester of 4-hydroxybenzoic acid or the corresponding sodium salts (methyl-, ethyl-, propyl- or butylparaben) and the like.

In order to increase the viscosity of the composition and thereby to make an effective contribution to the formation and maintenance of a homogeneous suspension, it may be advantageous to add a thickener; this can be added in an amount of up to about 10% by weight of the contents of the capsule. The thickening agent can be, for example, an inorganic substance, such as highly disperse silicon dioxide (for example the product Aerosil® from Degussa AG, Frankfurt am Main FRG), or an organic substance, such as agar-agar, acacia gum (gum arabic), tragacanth gum, pectins, starch, dextrins, cellulose ethers and the like.

If desired, the mechanical strength of the matrix formed can be increased by addition of a suitable agent. Lactose, for example, can be used as such an agent, and can be added to the composition in a weight ratio of up to 60%.

The pharmaceutical active ingredient which can be brought into the form of a hard gelatin capsule in this way can be, inter alia: an alpha-receptor blocker, such as dihydroergotamine and the hydrogenated derivatives of the secale alkaloids, tolazoline and phentolamine; a beta-receptor blocker, such as propranolol, acebutolol, oxyprenolol or pindolol; a sympathicomimetic, such as dopamine and the amphetamines; an analgesic, such as glafenine, acetylsalicylic acid, phenacetine and aminophenazone; an aldosterone antagonist, such as spironolactone; an agent against blood platelet agglutination, such as ticlopidine; an agent against angina pectoris, such as nitroglycerin and isosorbide dinitrate; an agent against asthma, such as theophylline and its derivatives; an antidepressant, such as imipramine, desipramine and amineptine; an antihistamine, such as pheniramine, thenalidine, thenyldiamine, ketotiphen, cyproheptadine and azatadine; an antihypertensive, such as methyldopa and prazosin; an antiinflammatory drug, such as ibuprofen, naproxen, diclofenac, indometacin, phenylbutazone, oxyphenbutazone and mefenamic acid; an anti-Parkinson agent, such as trihexyphenidine, orphenadrine and ethopropazine; a tranquilizer, such as meprobamate, lorazepam, diazepam and chlordiazepoxide; a bronchodilator and antiasthmatic, such as isoprenaline and salbutamol; a diuretic, such as chlorothiazide, hydrochlorothiazide, furosemide and triamterene; a calcium antagonist, such as nifedipine, diltiazem, verapamil, bepridil, perhexiline and prenylamine; and a neuroleptic, such as the phenothiazine, butyrophenone, thioxanthene and substituted benzamide derivatives, and the like.

According to the invention, the capsules described are prepared by heating the nonionic surfactant or the mixture of such surfactants to a temperature above the melting point or softening point thereof, mixing first the organic polymer or polymers and then the active ingredient with the molten mass, while maintaining the temperatures already stated and with stirring, until a homogeneous liquid composition is formed, removing the air remaining in the composition and filling hard gelatin capsules with the amount of liquid composition corresponding to the dose of active ingredient envisaged for one capsule. At the end of the filling operation, the liquid composition solidifies increasingly to form a solid composition, either by being left to stand at room temperature or by cooling.

According to the invention, hard gelatin capsules which, as a result of the regular flow and permanent homogeneity of the formulation, allow problem-free preparation on an industrial scale, do not become brittle and fragile during storage, contain considerable amounts of the active ingredient and release the active ingredient in the organism over a relatively long period of time are thus provided for the first time.

As was already generally known, an active ingredient which is slightly soluble in water is released very rapidly from its mixture with a hydrophilic substance when the mixture is brought into contact with water or an aqueous medium; a mixture of ibuprofen and a polyethylene glycol (PEG) may be mentioned as an example. On the other hand, the same active ingredient is released only slowly from a mixture with a lipophilic substance.

Surprisingly, it has now been found that the manner of the release changes completely and reverses in sense if the mixture of active ingredient which is insoluble or slightly soluble in water and hydrophilic surfactant is mixed with an organic polymer which is miscible with both components together.

For example, Table 1 shows the release of the slightly soluble active ingredient ibuprofen from a mixture with the very hydrophilic PEG 1500-stearate or the less hydrophilic PEG 300-stearate: in the first case, 97% is released in 0.25 hour, and in the second case 98.1% is released in 1 hour. If the polymer Eudragit® S 100 is now added to both mixtures, an impressive delay in the release is to be observed: 84.8% is released in 8 hours and, respectively, 91.4% is released in 2 hours. In the case of the more strongly hydrophilic surfactant (HLB=17), the delay, i.e. the reversal in the release operation, is significantly greater than in the case of the less hydrophilic surfactant (HLB=9 to 10).

These conditions and their reversal by addition of an organic polymer are illustrated by FIG. 1 for active ingredients which are slightly soluble or insoluble in water. Curves A and B show the rate of release of the active ingredient for a surfactant of a particular HLB value in the absence (A) and in the presence (B) of an organic polymer. This rate is expressed as the total amount of active ingredient, in % by weight of the initial content, which has been released after each unit of time (% by weight per hour).

TABLE 1

|  | For comparison | Example 1 | For comparison | Example 2 |
|---|---|---|---|---|
| Ibuprofen | 60.0 | 60.0 | 60.0 | 60.0 |
| Stearate 1500 | 40.0 } HLB = 17 | 37.4 } HLB = 17 | — } HLB = 9–10 | — } HLB = 9–10 |
| Stearate 300 | — | — | 40.0 | 37.4 |
| Eudragit S 100 | — | 26 | — | 2.6 |
| Time in hours | Amount of active ingredient released, cumulative values in % by weight | | | |
| 0 | 0 | 0 | 0 | 0 |

TABLE 1-continued

|     | For comparison | Example 1 | For comparison | Example 2 |
|-----|----------------|-----------|----------------|-----------|
| 0.1 | 20.8           | —         | 8.3            | 7.2       |
| 0.25| 97             | —         | 33.2           | 22.5      |
| 0.5 | —              | —         | 69.9           | 43.7      |
| 1   | —              | 20.3      | 98.1           | 74.5      |
| 2   | —              | 34.2      | —              | 91.4      |
| 4   | —              | 57.8      |                | —         |
| 6   | —              | 69.9      |                | —         |
| 8   | —              | 84.8      |                | —         |

A corresponding reversal in the conditions does not take place with water-soluble active ingredients. These are released rapidly or relatively rapidly from a mixture with a surfactant; the rate of release increases with the hydrophilic character of the surfactant. They are thus released comparatively more slowly from a mixture with a hydrophobic surfactant. The addition of an organic polymer thus in all cases causes a significant delay in the release.

This is illustrated by the example of the very readily soluble diltiazem.HCl in Table 2. In the absence of a polymer 92.5% is released in 1.5 hours; the addition of ethylcellulose delays the release considerably, as can be seen from Examples 3, 4 and 5. When these examples are compared with one another, it is also seen that the retarding effect is all the more pronounced the more hydrophobic the surfactant mixture: at an HLB of 10.5, 68.5% of the active ingredient is released in 6 hours, whereas at an HLB of 11.5, 84.5% is released in 3 hours.

Figure 2:
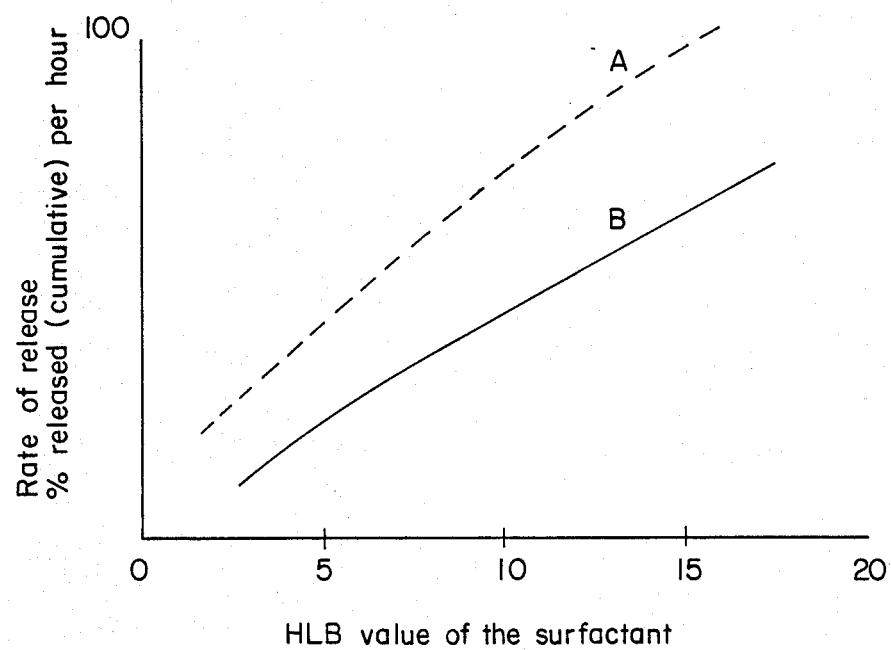

These circumstances are illustrated by FIG. 2 for active ingredients which are soluble in water. Curves A and B represent the rate of release of the active ingredient for a surfactant of a particular HLB value in the absence (A) and in the presence (B) of an organic polymer.

TABLE 2

|              | For comparison | Example 3 | Example 4 | Example 5 |
|--------------|----------------|-----------|-----------|-----------|
| Diltiazem.HCl | 21.0          | 21.0      | 21.0      | 21.0      |
| Stearate 400 | 55.3 } HBL =   | 69.0 } HLB ca. | 48.3 } HLB ca. | 34.5 } HLB ca. |
| Stearate 300 | 23.7 } 10.9    | — } 11.5  | 20.7 } 10.9 | 34.5 } 10.5 |
| Ethylcellulose | —            | 10.0      | 10.0      | 10.0      |

| Time in hours | Amount of active ingredient released, cumulative values in % by weight | | | |
|---|---|---|---|---|
| 0   | 0    | 0    | 0    | 0    |
| 0.5 | 44.4 | 17.5 | 11.5 | 12.1 |
| 1   | 77.3 | 28.5 | 17.6 | 20.5 |
| 1.5 | 92.5 | —    | —    | —    |
| 2   | —    | 54.1 | 30.0 | 34.1 |
| 3   | —    | 84.5 | 48.4 | 44.6 |
| 4   | —    | —    | 66.7 | 54.7 |
| 5   | —    | —    | 82.4 | 62.8 |
| 6   | —    | —    | 95.1 | 68.5 |

Furthermore, it has proved to be possible to control the degree of release within certain limits not only by the choice of surfactant or surfactant mixture but also by changing the content of organic polymer. From Table 3, it can be seen that the reduction in the content of Eudragit ® S 100 by half results in a considerable reduction in the retarding effect: the amount of active ingredient released goes from 84.8% in 8 hours back to about 100% in 4 hours.

The change in the content of organic polymer, however, has an effect on the delay in the release of active ingredient only within certain limits. It can be seen from Table 4 that an increase in the polymer content beyond a certain value causes no further increase in delay or can even have an adverse effect. The content of organic polymers in the composition should therefore preferably be from 2 to 3% as the lower limit up to about 20% as the upper limit.

TABLE 3

|               | For comparison | Example 1 | Example 6 |
|---------------|----------------|-----------|-----------|
| Iuprofen      | 60.0           | 60.0      | 60.0      |
| Stearate 1500 | 40.0           | 37.4      | 38.68     |
| Eudragit S 100 | —             | 2.6       | 1.32      |

| Time in hours | Amount of active ingredient released, cumulative values in % by weight | | |
|---|---|---|---|
| 0    | 0    | 0     | 0     |
| 0.1  | 20.8 | —     | —     |
| 0.25 | 97   | —     | —     |
| 1    | —    | 20.3  | 29.32 |
| 2    | —    | 34.2  | 59.6  |
| 4    | —    | 57.8  | 98.1  |
| 6    | —    | 69.9  | 100.5 |
| 8    | —    | 84.8  | 101.0 |

TABLE 4

|               | For comparison | Example 7 | Example 8 |
|---------------|----------------|-----------|-----------|
| Verapamil.HCl | 25.0           | 25.0      | 25.0      |
| Stearate 1500 | 75.0           | 67.0      | 62.0      |
| Eudragit S 100 | —             | 8.0       | 13.0      |

| Time in hours | Amount of active ingredient released, cumulative values in % by weight | | |
|---|---|---|---|
| 0   | 0    | 0    | 0    |
| 0.1 | 39.8 | —    | —    |
| 0.5 | 98.3 | —    | —    |
| 1   | —    | 26.0 | 33.9 |
| 2   | —    | 41.5 | 46.5 |
| 4   | —    | 61.0 | 67.5 |
| 6   | —    | 75.0 | 85.9 |
| 8   | —    | 85.0 | 95.8 |

In general, a more rapid release of the active ingredient is observed if its concentration in a pharmaceutical formulation is increased. If the concentration or the content of a slightly soluble or insoluble active ingredient in the capsules according to the invention is increased, in contrast, completely against expectations, a slowing down in the release of active ingredient is observed. This is clearly seen from Table 5: at a constant content of organic polymer and with an increase in the active ingredient content from 20% to 40% and 60%, the delay in release increases from 54.15% to 30.09% and finally 20.88%—in each case in 8 hours. This astonishing reversal of the conditions previously observed only applies, however, to insoluble or slightly soluble active ingredients.

TABLE 5

|  | For comparison | Example 9 | Example 10 | Example 11 |
|---|---|---|---|---|
| Ibuprofen | 60.0 | 20.0 | 40.0 | 60.0 |
| Stearate 4000 | 40.0 | 77.0 | 57.0 | 37.0 |
| Eudragit S 100 | — | 3.0 | 3.0 | 3.0 |
| Time in hours | Amount of active ingredient released, cumulative values in % by weight | | | |
| 0 | 0 | 0 | 0 | 0 |
| 0.1 | 18.0 | — | — | — |
| 0.25 | 78.5 | — | — | — |
| 1 | 98.9 | 25.46 | 12.1 | 8.2 |
| 2 |  | 39.38 | 16.67 | 11.81 |
| 4 |  | 45.79 | 21.95 | 15.69 |
| 6 |  | 51.1 | 26.34 | 18.7 |
| 8 |  | 54.15 | 30.09 | 20.88 |

GENERAL PREPARATION INSTRUCTIONS

The nonionic surfactant or mixture of such surfactants is taken in a vessel which can be heated and is brought to the molten state by heating to about 50° C. The organic polymer is added to the molten mass and the mixture is stirred until the organic polymer has dissolved completely or until a uniform suspension has formed. The active ingredient is then added, the mixture is stirred until a uniform suspension has formed and any air included is removed by leaving the composition to stand in a vacuum chamber. All the process measures are carried out at a temperature of about 50° C. Finally, hard gelatin capsules are filled with the calculated amount of the resulting composition.

In Example 12, the composition does not contain isosorbide dinitcate as such, because handling of this active ingredient is associated with a risk of explosion. It is therefore as a rule used in the form of a mixture with an inert diluent, in the present case as a mixture (20:30) with lactose. This mixture, instead of the isosorbide dinitrate itself, is therefore added to the transparent molten composition obtained after addition of Eudragit S 100.

EXAMPLE 12

10,000 capsules each containing 60 mg of isosorbide dinitrate are prepared starting from the following substances; the weight ratio of the relevant components in the formulation is shown in parentheses:

| Stearate 1500 | 2.090 kg (55%) |
|---|---|
| Eudragit S 100 | 0.190 kg (5%) |
| Isosorbide dinitrate/lactose (40:60) | 1.520 kg (40%) |

Exactly 2.090 kg of stearate 1500 are taken in a jacketed flask equipped with a stirring device and a vacuum connection and the flask is heated to 55° C., and kept at this temperature, by means of a water circulation controlled by a thermostat. When all the stearate 1500 has melted, the stirrer is switched on at a speed of 15 revolutions/minute and exactly 190 g of Eudragit S 100 are added. A vacuum is applied to the flask, while maintaining the temperature at 55° C., and stirring is continued until the Eudragit S 100 has completely dissolved in the stearate 1500 and air bubbles can no longer be seen in the solution.

Exactly 1.520 kg of the isosorbide dinitrate/lactose mixture in a weight ratio of 40:60 are weighed out and added to the solution previously obtained. The temperature of the flask is kept at 55° C. and the mixture is stirred under a vacuum for one hour at 15 revolutions/minute. If the resulting mixture appears to form air bubbles or too much foam, stirring is continued at 55° C. in vacuo until all the air has been removed. The mixture is then introduced into the hopper of a filling device for hard gelatin capsules (for example model HK-400 from Robert Bosch GmbH, Waiblingen/FRG) and size 1 capsules are each filled with 380 mg of the molten composition.

In the dissolving test, the capsules obtained show a remarkable delay in the release of active ingredient, as can be seen from the following table.

TABLE 6

| Time in hours | Amount of isosorbide dinitrate released, cumulative values in % by weight |
|---|---|
| 0.5 | 9.2 |
| 1.0 | 17.5 |
| 2.0 | 20.5 |
| 4.0 | 27.9 |
| 6.0 | 35.5 |
| 8.0 | 43.8 |

Determination of the rate of release

For each example, the rate with which the active ingredient is released from the capsule in water was measured. For this, the customary dissolving method described under the title "Dissolution Paddle Apparatus" in U.S. Pharmacopoeia XX (1979) on page 959 was used.

For this purpose, the total amount of active ingredient released (cumulative values) is determined after fixed periods of time, in particular after 1, 2, 4, 6 and 8 hours, and this amount is expressed in % by weight of the amount of active ingredient contained in the capsule. The resulting cumulative values are given in the tables.

The abbreviations in the examples have the following meanings:

Stearate 4000: the palmitostearate of polyoxyethylene glycol 4000, a very hydrophilic compound, HLB value above 19

Stearate 1500: the palmitostearate of polyoxyethylene glycol 1500, HLB value 17

Stearate 400: the palmitostearate of a polyoxyethylene glycol of lower molecular weight, significantly less hydrophilic, HLB value 11 to 12

Stearate 300: the distearate of polyoxyethylene glycol 300, even less hydrophilic, HLB value 9 to 10

Eudragit ® S 100: an acrylic resin consisting of methacrylic acid and methyl methacrylate (manufacturer: Röhm Pharma GmbH, Darmstadt/FRG)

Eudragit ® RS PM: a mixture of acrylic acid ester and methacrylic acid ester copolymers with a low content of quaternary ammonium groups, containing 0.5% of talc; supplied as a powder composition with a particle size of less than 0.315 mm for at least 90% and less than 1.0 mm for at least 99% (manufacturer: Röhm Pharma GmbH, Darmstadt/FRG)

Ibuprofen: 2-(4-isobutylphenyl)-propionic acid

Diltiazem.HCl: 3-acetoxy-5-(2-dimethylaminoethyl)-2,3-dihydro-2-(4-methoxyphenyl)-1,5-benzothiazepin-4(5H)-one hydrochloride Verapamil.HCl: 5-N-(3,4-dimethoxyphenethyl)-N-methylamino-2-(3,4-dimethoxyphenyl)-2-isopropyl-valeronitrile hydrochloride In addition to the dissolving test, the bioavailability of representative capsules according to the invention was investigated in comparison with that of a commercial product of the same class; capsules of the following composition were used for this.

| Verapamil capsules 2 KL 917 | | |
|---|---|---|
| Stearate 400 | 79.7 mg | 18.6% |
| Stearate 300 | 186.0 | 43.4 |
| Ethylcellulose N 10 | 42.8 | 10.0 |
| Verapamil.HCl | 120.0 | 28.0 |
| | 428.5 mg | 100% |
| Verapamil capsules 4 KL 937 (according to Example 8) | | |
| Stearate 1500 | 297.6 mg | 62.0% |
| Eudragit ® RS PM | 62.4 | 13.0 |
| Verapamil.HCl | 120.0 | 25.0 |
| | 480.0 mg | 100% |

The investigation was carried out by Ian W. French and Associates Ltd., Markham (Ontario, Canada) in January 1986 on six healthy male volunteers aged 18 to 40 years. Each volunteer received one capsule of each of the two formulae once at an interval of one week. Blood samples at the time 0 and at 1, 2, 3, 4, 6, 8, 10, 12, 16 and 24 hours after administration of the capsule were taken to determine the verapamil concentration in the blood plasma. The results of the determinations are shown in the following table.

by a $T_{max}$ value of about 7 hours, is achieved approximately equally well by both formulations. In the comparison preparation, the $C_{max}$ value is higher and the curve of the verapamil concentration—with about the same AUC value—is steeper and also drops more steeply; the retarding effect of the Isoptin tablets is thus less pronounced.

Summarizing, it can be said that the investigation of the bioavailability in accordance with the strict methods of testing used in clinical trials has entirely confirmed the retarding effect which has been demonstrated for the capsules according to the invention on investigation of the delay in the release of the active ingredient in vitro.

I claim:

1. A medicament exhibiting a delayed release of active ingredient in the form of hard gelatin capsules which comprises:
    an active ingredient;
    a surfactant ingredient which comprises polyglycol ethers, esters of mixtures thereof, which has both hydrophilic and lipophilic portions and is chosen based on the relative water
    solubility or water insolubility of said active ingredient,
    wherein said solubility or insolubility is defined as follows:

| Solubility | Parts of Solvent Required for 1 Part of Solution |
|---|---|
| very readily soluble | less than 1 |
| readily soluble | from 1 to 10 |
| soluble | from 10 to 30 |
| sparingly soluble | from 30 to 100 |
| slightly soluble | from 100 to 1000 |
| very slightly soluble | from 1000 to 10,000 |
| practically insoluble or insoluble | 10,000 and more, |

TABLE 7

| Time of blood withdrawal (in hours) | Capsules 4 KL 937 (1 × 120 mg Verapamil) | Capsules 2 KL 917 (1 × 120 mg Verapamil) | Tablets Isoptin-Retard* (1 × 120 mg Isoptin) |
|---|---|---|---|
| | Average verapamil concentration in the blood plasma (in ng/ml) | | |
| 0 | 0 | 0 | 0 |
| 1.0 | 0 | 5.37 ± 8.71 | 1.89 ± 4.24 |
| 2.0 | 4.16 ± 4.62 | 14.98 ± 5.17 | 7.26 ± 8.15 |
| 3.0 | 9.22 ± 9.01 | 18.02 ± 13.09 | 20.09 ± 21.71 |
| 4.0 | 14.02 ± 18.39 | 20.90 ± 14.38 | 27.67 ± 27.10 |
| 6.0 | 22.94 ± 19.97 | 20.66 ± 15.32 | 30.00 ± 14.70 |
| 8.0 | 21.82 ± 11.49 | 15.64 ± 14.37 | 21.70 ± 9.78 |
| 10.0 | 16.02 ± 8.47 | 15.41 ± 10.08 | 18.26 ± 8.08 |
| 12.0 | 12.48 ± 9.63 | 12.87 ± 9.02 | 12.51 ± 7.73 |
| 16.0 | 9.99 ± 7.19 | 8.86 ± 11.66 | 4.61 ± 5.52 |
| 24.0 | 3.63 ± 5.80 | 3.61 ± 5.66 | 1.31 ± 3.21 |
| Pharmacokinetic parameters | | | |
| AUC 0-24 hours (ng · hours/ml) | 269.82 ± 154.62 | 276.81 ± 101.46 | 281.95 ± 141.77 |
| $C_{max}$ (ng/ml) | 29.34 ± 16.38 | 33.78 ± 7.19 | 38.78 ± 23.14 |
| $T_{max}$ (hours) | 7.00 ± 3.74 | 7.17 ± 5.00 | 6.33 ± 2.94 |

AUC: area under the curve
$C_{max}$: maximum concentration in the plasma
$T_{max}$: time of the maximum concentration
*Manufacturer: Knoll AG, Ludwigshafen/FRG These results show that the capsules of the two compositions described above are entirely comparable to one another in respect of the AUC and $C_{max}$; ie. in respect of absorption or bioavailability of the active ingredient. They furthermore show that the retarding effect, i.e. the slow and lasting release of the active ingredient in the organism, as manifested in particular said surfactant ingredient having the following hydrophilipophilic balance (HLB) value,
    above 16 for an active ingredient which is insoluble or slightly soluble in water, between 16 and 10 for an active ingredient which is sparingly soluble in water, and less than 10 for an active ingredient which is soluble in water; and an organic polymer or polymers which form a homogeneous solution or suspension with said active ingredient and said surfactant ingredient, the solution or suspension being in free-flowing form below about 70° C., wherein said active ingredient is in an amount of about 1 to 60%, said surfactant ingredient is in an amount of about 30 to 90% and said organic polymer is in an amount of about 1 to 45% of the weight of the contents of the capsule.

2. A medicament as claimed in claim 1, wherein said surfactant ingredient is a polyoxyethylene glycol fatty acid ester a polyoxyethylene glycol fatty alcohol ether or a fatty acid ester of sorbitan etherified by polyoxyethylene glycol.

3. A medicament as claimed in claim 2, wherein said surfactant ingredient is the palmitostearate of a polyoxyethylene glycol having the following molecular weight: 4000, for an HLB value above 19; 1500, for an HLB value of 17; or 400, for an HLB value of 11 to 12; polyoxyethylene glycol 300-distearate for an HLB value of 9 to 10; the laurate, palmitate, stearate or oleate of sorbitan etherified by 4 mol of polyoxyetheyne glycol, or a mixture of two or more of these compounds.

4. A medicament as claimed in claim 2, wherein said surfactant ingredient is a polyoxyethylene glycol ether of lauryl alcohol, cetyl alcohol, stearyl alcohol or oleyl alcohol or a mixture of two or more of these compounds.

5. A medicament as claimed in claim 1, wherein said organic polymer is methyl polyacrylate, methyl polymethacrylate, ethylcellulose, methylcellulose or a mixture of two or more of these compounds.

6. A medicament exhibiting a delayed release of active ingredient in the form of hard gelatin capsules which consists essentially of:

an active ingredient;

a surfactant ingredient which comprises polyglycol ethers, esters or mixtures thereof, which has both hydrophilic and lipophilic portions and is chosen baed on the relative water solubility or water insolubility of said active ingredient, wherein said solubility or insolubility is defined as follows:

| Solubility | Parts of Solvent Required for 1 Part of Solution |
|---|---|
| very readily soluble | less than 1 |
| readily soluble | from 1 to 10 |
| soluble | from 10 to 30 |
| sparingly soluble | from 30 to 100 |
| slightly soluble | from 100 to 1000 |
| very slightly soluble | from 1000 to 10,000 |
| practically insoluble or insoluble | 10,000 and more, | said surfactant ingredient having the following hydrophilic-lipophilic balance (HLB) value, above 16 for an active ingredient which is insoluble or slightly soluble in water, between 16 and 10 for an active ingredient which is sparingly soluble in water, and less than 10 for an active ingredient which is soluble in water; and an organic polymer or polymers which form a homogeneous solution or suspension with said active ingredient and said surfactant ingredient, the solution or suspension being in free-flowing form below about 70° C., wherein said active ingredient is in an amount of about 1 to 60%, said surfactant ingredient is in an amount of about 30 to 90% and said organic polymer is in an amount of about 1 to 45% of the weight of the contents of the capsule.

7. A medicament as claimed in claim 1 wherein the capsules also contain as an antioxidant or stabilizer tert.-butyl-4-methoxyphenol, 2,6-di-tert.-butyl-4-methoxyphenol, octyl gallate, dodecyl gallate, lactic acid or its sodium salt, or the methyl, ethyl, propyl or butyl ester of 4-hydroxybenzoic acid or the corresponding sodium salts thereof.

8. A medicament as claimed in claim 1, wherein the capsules also contain as a thickening agent highly disperse silicon dioxide, agar-agar, acacic gum, tragacanth gum, pectins, starch, dextrins or cellulose esters.

9. A medicament as claimed in claim 1, wherein the capsules also contain lactose as an agent for increasing the mechanical strength of the contents.

10. A process for the preparation of a medicament exhibiting a delayed release of active ingredient in the form of hard gelatin capsules, wherein said medicament comprises:

an active ingredient;

a surfactant ingredient which comprises polyglycol ethers, esters or mixtures thereof, which has both hydrophilic and lipophilic portions and is chosen based on the relative water solubility or water insolubility of said active ingredient, wherein said solubility or insolubility is defined as follows:

| Solubility | Parts of Solvent Required for 1 Part of Solution |
|---|---|
| very readily soluble | less than 1 |
| readily soluble | from 1 to 10 |
| soluble | from 10 to 30 |
| sparingly soluble | from 30 to 100 |
| slightly soluble | from 100 to 1000 |
| very slightly soluble | from 1000 to 10,000 |
| practically insoluble or insoluble | 10,000 and more, | said surfactant ingredient having the following hydrophilic-lipophilic balance (HLB) value, above 16 for an active ingredient which is insoluble or slight soluble in water, between 16 and 10 for an active ingredient which is sparingly soluble in water, and less than 10 for an active ingredient which is soluble in water; and an organic polymer or polymers which form a homogeneous solution or suspension with said active ingredient and said surfactant ingredient, the solution or suspension being in free-flowing form below about 70° C., wherein said active ingredient is in an amount of about 1 to 60%, said surfactant ingredient is in an amount of about 30 to 90% and said organic polymer is in an amount of about 1 to 45% of the weight of the contents of the capsule, said process comprising the steps of:

bringing said surfactant ingredient to the state of a molten mass by heating to a temperature above the melting point or softening point thereof, mixing first said organic polymer or polymers and then said active ingredient with said molten mass, while maintaining the temperature already stated and with stirring, until a homogeneous liquid composition is formed, vacuum removing the air remaining in said liquid composition, and filling hard gelatin capsules with an amount of said liquid composition corresponding a predetermined dose of active ingredient envisaged for one capsule.

11. A medicament as claimed in claim 2, wherein said organic polymer is methyl polyacrylate, methyl polymethacrylate, ethylcellulose, methylcellulose or a mixture of two or more of these compounds.

12. A medicament as claimed in claim 11, wherein the capsules also contain lactose as an agent for increasing the mechanical strength of the contents.

13. A medicament as claimed in claim 3, wherein said organic polymer is methyl polyacrylate, methyl polymethacrylate, ethylcellulose, methylcellulose or a mixture of two or more of these compounds.

14. A medicament as claimed in claim 4, wherein said organic polymer is methyl polyacrylate, methyl polymethacrylate, ethylcellulose, methylcellulose or a mixture of two or more of these compounds.

15. A medicament as claimed in claim 2, wherein the capsules also contain as an antioxidant or stabilizer tert.-butyl-4-methyxoyphenol, 2,6-di-tert.-butyl-4-methoxyphenol, octyl gallate, dodecyl gallate, lactic acid or its sodium salt, or the methyl, ethyl, propyl or butyl ester of 4-hydroxybenzoic acid or the corresponding sodium salts thereof.

16. A medicament as claimed in claim 5, wherein the capsules also contain as an antioxidant or stabilizer tert.-butyl-4-methoxyphenol, 2,6-di-tert.-butyl-4-methoxyphenol, octyl gallate, dodecyl gallate, laotic acid or its sodium salt, or the methyl, ethyl, propyl or butyl ester of 4-hydroxybenzoic acid or the corresponding sodium salts thereof.

17. A medicament as claimed in claim 12, wherein the capsules also contain as an antioxidant or stabilizer tert.-butyl-4-methoxyphenol, 2,6-di-tert.-butyl-4-methoxyphenol, octyl gallate, dodecyl gallate, lactic acid or its sodium salt, or the methyl, ethyl, propyl or butyl ester of 4-hydroxybenzoic acid or the correspond sodium salts thereof.

18. A medicament as claimed in claim 2, wherein the capsules also contain as a thicknening agent highly disperse silicon dioxide, agar-agar, acacia gum, traganeanth gum, pectins, starch, dextrins or cellulose esters.

19. A medicament as claimed in claim 5, wherein the capsules also contain as a thickening agent highly disperse silicon dioxide, agar-agar, acacia gum, traygacanth gum, pectins, starch, dextrins or cellulose esters.

20. A medicament as claimed in claim 12, wherein the capsules also contain as a thickening agent highly disperse silicon dioxide, agar-agar, acacia gum, tragacanth gum, pectins, starch, dextrins or cellulose esters.

21. A medicament as claimed in claim 2, wherein the capsules also contain lactose as an agent for increasing the mechanical strength of the contents.

22. A medicament as claimed in claim 5, wherein the capsules also contain lactose as an agent for increasing the mechanical strength of the contents.

* * * * *